United States Patent [19]

Abou-Gharbia

[11] Patent Number: 4,804,751
[45] Date of Patent: Feb. 14, 1989

[54] POLYCYCLIC HYDROCARBON SUCCINIMIDES WITH PSYCHOTROPIC ACTIVITY

[75] Inventor: Magid A. Abou-Gharbia, Wilmington, Del.

[73] Assignee: American Home Products Corporation, New York, N.Y.

[21] Appl. No.: 68,470

[22] Filed: Jun. 30, 1987

[51] Int. Cl.$^4$ ................ A61K 31/495; C07D 401/06; C07D 401/14
[52] U.S. Cl. .................................. 540/575; 544/238; 544/239; 544/295; 544/300; 544/357; 544/360; 544/364; 544/372; 549/234
[58] Field of Search ............ 544/238, 239, 295, 300, 544/357, 360, 364, 372; 540/575

[56] References Cited

U.S. PATENT DOCUMENTS

| | | | |
|---|---|---|---|
| 4,479,954 | 10/1984 | Hirose | 540/575 |
| 4,562,255 | 12/1985 | Freed | 544/357 |
| 4,567,180 | 1/1986 | Hirose | 544/364 |
| 4,663,456 | 5/1987 | Abou-Gharbia | 544/357 |
| 4,732,983 | 3/1988 | Stack | 544/295 |
| 4,732,984 | 3/1988 | Abou-Gharbia | 544/238 |
| 4,737,500 | 4/1988 | Sorg | 544/364 |
| 4,748,240 | 3/1988 | Stack | 544/295 |
| 4,757,073 | 7/1988 | New | 544/364 |

FOREIGN PATENT DOCUMENTS 200968 11/1986 European Pat. Off. ............ 544/360

OTHER PUBLICATIONS

Edman, J. Org. Chem (1968), 33(10), pp. 3808–3816.

Primary Examiner—Donald G. Daus
Assistant Examiner—Mark W. Noel
Attorney, Agent, or Firm—George Tarnowski

[57] ABSTRACT

There are disclosed compounds of the formula

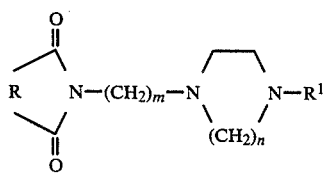

wherein R represents 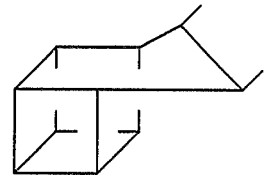

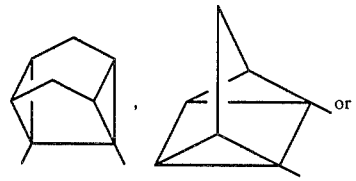

in which Y and Z are both 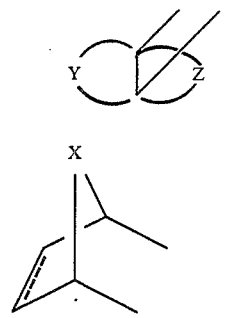

where X is methylene, ethylene or O and the dotted line represents an optional double bond, or one of Y or Z is

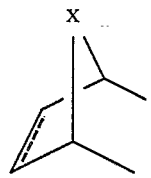

and the other represents $-(CH_2)_o-$ or

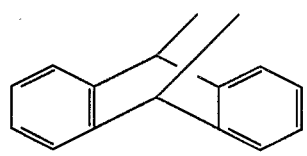

$R^1$ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro, hydroxy and trifluoromethyl;
m is 2–4;
n is 1–3;
o is 1–5;
and the pharmaceutically acceptable salts thereof and their use as antipsychotic/anxiolytic agents having a low liability for extrapyramidal side effects.

7 Claims, No Drawings

POLYCYCLIC HYDROCARBON SUCCINIMIDES WITH PSYCHOTROPIC ACTIVITY

This invention relates to novel compounds having antipsychotic activity and being characterized by the general formula

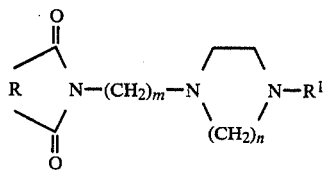

wherein R represents

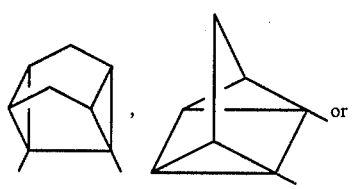

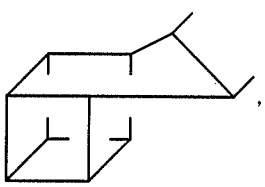, or in which Y and Z are both

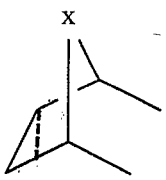

where X is methylene, ethylene or O and the dotted line represents an optional double bond, or one of Y or Z is

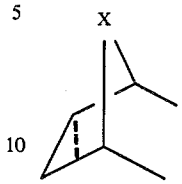

and the other represents —$(CH_2)_o$— or

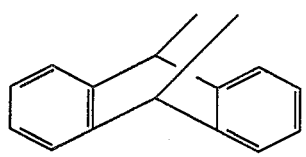

$R^1$ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro, hydroxy and trifluoromethyl;

m is 2-4;
n is 1-3;
o is 1-5;

and the pharmaceutically acceptable salts thereof.

The terms "lower alkyl" and "lower alkoxy" refer to moieties having 1-6 carbon atoms in the carbon chain. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention can be prepared according to the following reaction scheme, in which an appropriate tetrasubstituted polycyclic succinic anhydride is reacted with an appropriately substituted N-(4-aminoloweralkyl)-N-heterocyclic substituted diazacycle, for example, as follows:

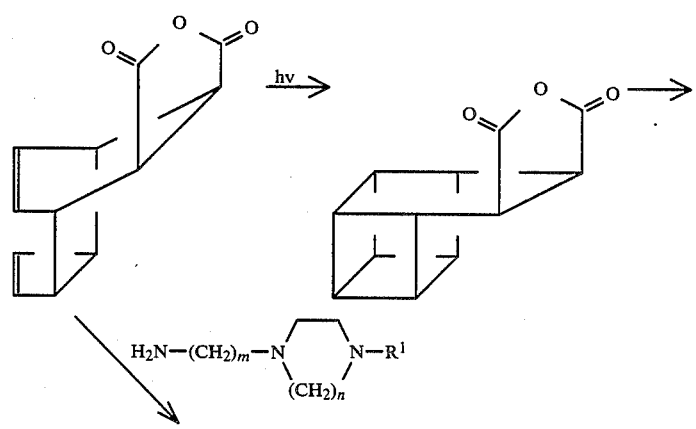

-continued

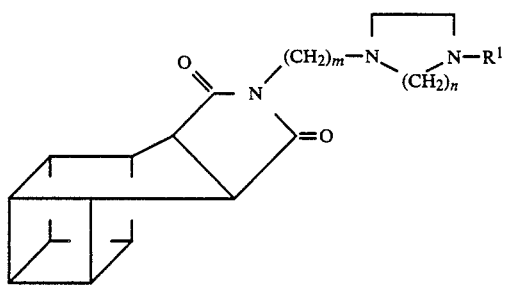

The starting pentacyclo[4.4.0.0$^{2,5}$.0$^{3,8}$.0$^{4,7}$]decane-9,10-dicarboxylic acid anhydride used in the above-illustrated reaction sequence can be prepared according to the method of Cuts et al. disclosed in "Organic Photochemical Syntheses," Vol. 1, p. 83–4 (John Wiley and Sons, Inc., 1971).

In an identical manner, other compounds within the scope of the invention can be prepared using appropriate starting anhydrides. Thus, the anhydride

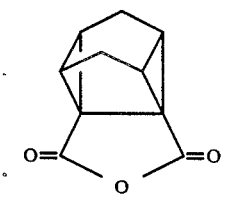

can be prepared by the method of Takahashi, *Tetrahedron Letters*, 30, 3387–3390 (1968). And the following anhydrides can be prepared according to the procedures taught by Edman and Simmons, *J. Org. Chem.*, 33, 3808–3816 (1968):

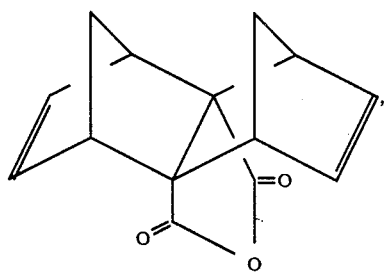

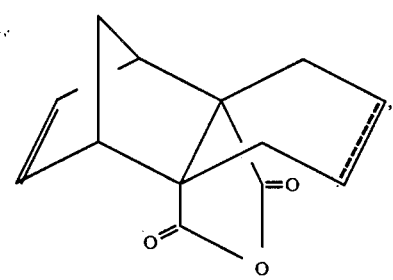

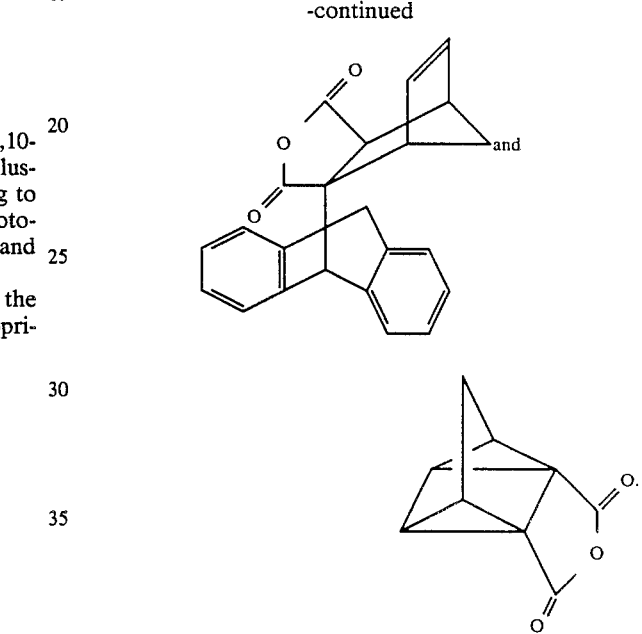

Other starting materials are available commercially or can be made by other procedures taught in the chemical literature.

The saturated analogs of the compounds prepared from the above starting anhydrides can be prepared by hydrogenating the intermediates or final products using hydrogen and Pd/C as a catalyst.

Of course, other methods of preparation, which will occur to those skilled in the art, may also be employed to prepare the compounds of the invention.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro-[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/anti-psychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

1,4,5,8-Tetrahydro-10-[4-[4-(2-pyrimidinyl-1-piperazinyl]butyl]-4a,8a-(methaniminomethano)-1,4:5,8-dimethanonaphthalene-9,11-dione, dihydrochloride, hemihydrate A mixture of 1,4,4A,5,8,8A-hexahydro-1,4:5,8-dimethanonaphthalene-4A,8A-dicarboxylic anhydride 4.5 g (0.02 mol), 1-(4-aminobutyl)-4-(2-pyrimidinyl)-piperazine 4.8 g (0.02 mol) and 50 mL of pyridine is refluxed overnight. The solvent is removed under reduced pressure and the remaining oil is purified by HPLC using ethyl acetate as an eluent. The title compound is converted to the hydrochloride salt by dissolving in ethanol and adding 5 mL ethanol saturated with hydrogen chloride, m.p. 165°–166° C.

Analysis for: $C_{26}H_{31}N_5O_2 \cdot 2HCl \cdot \frac{1}{2}H_2O$. Calculated: C, 59.20; H, 6.45; N, 13.28. Found: C, 58.80; H, 6.48; N, 13.06.

EXAMPLE 2

10-[4-[4-(6-Chloro-2-pyrazinyl)-1-piperazinyl]butyl]-1,4,5,8-tetrahydro-4a,8a-(methaniminomethano)-1,4,:5,8-dimethanonaphthalene-9,11-dione, hydrochloride The title compound is prepared following the procedure of Example 1 using 1-(4-aminobutyl)-4-(6-chloro-2-pyrazinyl)piperazine instead of 1-(4-aminobutyl)-4-(2-pyrimidinyl)piperazine and is converted to the hydrochloride salt, m.p. 262°–266° C.

Analysis for: $C_{26}H_{30}ClN_5O_2 \cdot HCl$. Calculated: C, 60.34; H, 6.18; N, 13.53. Found: C, 59.77; H, 6.44; N, 13.34.

EXAMPLE 3

1,4,5,8-Tetrahydro-10-[4-[4-(2-pyrazinyl)-1-piperazinyl]butyl]-4a,8a-(methaniminomethano)-1,4:5,8-dimethanonaphthalene-9,11-dione, dihydrochloride, sesquihydrate The title compound is prepared following the procedure of Example 1 using 1-(4-aminobutyl)-4-(2-pyrazinyl)piperazine instead of 1-(4-aminobutyl)-4-(2-pyrimidinyl)piperazine and is converted to the hydrochloride salt; m.p. 272°–275° C.

Analysis for: $C_{26}H_{31}N_5O_2 \cdot 2HCl \cdot 1\frac{1}{2}H_2O$. Calculated: C, 57.24; H, 6.60; N, 12.84. Found: C, 56.89; H, 6.50; N, 12.84.

EXAMPLE 4

Octahydro-10-[4-[4-(2-pyrimdinyl)-1-piperazinyl]-butyl]-4a,8a-(methaniminomethano)-1,4:5,8-dimethanonaphthalene-9,11-dione, dihydrochloride The title compound is prepared following the procedure of Example 1 using 1,2,3,4,4A,5,6,7,8,8A-decahydro-1,4:5,8-dimethanonaphthene-4A,8A-dicarboxylic anhydride instead of 1,4,4A,5,8,8A-hexahydro-1,4:5,8-dimethanonaphthalene-4A,8A-dicarboxylic anhydride and is converted to the hydrochloride salt, m.p. 223°–225° C.

Analysis for: $C_{26}H_{35}N_5O_2 \cdot 2HCl$. Calculated: C, 59.31; H, 7.03; N, 13.30; Cl, 13.40. Found: C, 59.03; H, 7.15; N, 13.19; Cl, 13.42.

EXAMPLE 5

Octahydro-10-[4-[4-(6-chloro-2-pyrazinyl)-1-piperazinyl]butyl]-4a,8a-(methaniminomethano)-1,4:5,8-dimethanonaphthalene-9,11-dione, dihydrochloride, hemihydrate The title compound is prepared following the procedure of Example 1 using 1,2,3,4,4A,5,6,7,8,8A-decahydro-1,4:5,8-dimethanonaphthalene-4A,8A-dicarboxylic anhydride instead of 1,4,4A,5,8,8A-hexahydro-1,4:5,8-dimethanonaphthalene-4A,8A-dicarboxylic anhydride and 1-(4-aminobutyl)-4-(6-chloro-2-pyrazinyl)piperazine instead of 1-(4-aminobutyl)-4-(2-pyrimidinyl)piperazine and is converted to the hydrochloride salts, m.p. 244°–246° C.

Analysis for: $C_{26}H_{34}ClN_5O_2 \cdot 2HCl \cdot \frac{1}{2}H_2O$. Calculated: C, 55.17; H, 6.59; N, 12.38. Found: C, 55.15; H, 6.36; N, 12.41.

EXAMPLE 6

A test designed to determine the potential antipsychotic activity of the compounds of the invention is the conditioned avoidance (shelf-jump response) test.

This test is carried out as follows:

Male CD rats (Charles River) maintained at approximately 400-450 gm body weight are used. Previously trained rats are placed in plexiglass experimental chambers divided into two sections; a main chamber (10½"×6¾"×11⅜" high) and an elevated chamber or shelf (5⅞"×6¾"×5¾"). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculated the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding ($AB_{50}$) is obtained from a dose-effect regression line fitted by the method of least squares. Potential anti-psychotic compounds suppress avoidance responding and increase escape responding.

| Standard Compounds | $AB_{50}$ (mg/kg i.p.) |
|---|---|
| Haloperidol | 0.19 |
| Chlorpromazine | 3.69 |
| Clozapine | 6.94 |
| Buspirone | 9.94 |

The results for compounds of this invention in this test are presented in Table 1.

TABLE 1

| Compound of Example No. | Active at (mg/kg) |
|---|---|
| 1 | 40(i.p.) |
| 3 | 40(i.p.) |
| 4 | 40(i.p.) |

The results show that compounds of the invention are active intraperitoneally in this test.

EXAMPLE 7

The compounds of the invention are further studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The test is carried out as follows:

Several rats are decapitated and the brains are rapidly removed. Limbic brain tissue (nucleus accumbens, septal area, olfactory tubercle) is dissected and homoganized on ice in 9 volumes of buffer (50 mM Tris-HCl, 120 mN NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for three 15-sec bursts. The homogenate is then diluted 4-fold with buffer and centrifuged at 30,000×g for 20 minutes, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at −70° C. until use.

Thirty μL of the homogenate (0.2–0.3 mg protein/sample) are incubated with 0.3 nM $^3$H-spiroperidol (New England Nuclear) and various concentrations of test drug in a final volume of 1 ml of the above buffer for 10 minutes in a 37° C. water bath. At the end of the incubation, 3 ml of cold 50 mM Tris-HC-1, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 minutes with 10 ml of Hydrofluor (National Diagnostics) scintillation cocktail. The vials are then counted in a Packard 460CD scintillation counter.

Specific binding is defined as total binding less binding in the presence of 1 μM (+)butaclamol. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H-\text{Spiroperidol}]}{K_D}} \quad \text{where } K_D = 0.3 \text{ nM for spiroperidol binding}$$

| Standard Compounds | $K_i$ and 95% confidence interval |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention, and the prior art compound buspirone (8-[4-[4-(2-pyrimidinyl)-1-piperazinyl]butyl]-8-azapiro-[4.5]-decane-7,9-dione) in this assay are presented in Table 2.

TABLE 2

| Compound of Example No. | Limbic D-2 Binding ($K_i$ nM) |
|---|---|
| Buspirone | 119 |
| 1 | 53% inhibition at 1 μM |

TABLE 2-continued

| Compound of Example No. | Limbic D-2 Binding ($K_i$ nM) |
| --- | --- |
| 3 | 63% inhibition at 1 µM |

The results show that compounds of the invention display a very weak effect, evidencing a low potential for extrapyramidal side effects.

EXAMPLE 8

The ex vivo inhibition of 5-HT-1A serotonin receptor binding assay is used to determine whether the test compounds can cross the blood-brain barrier and affect the receptor in question and to give an indication of buspirone-like anxiolytic activity.

The assay is carried out as follows:

Several groups of rats (4-6 rats/group) are injected with test compound or the appropriate vehicle. Thirty minutes later, unless otherwise noted, rats are decapitated and their brains removed. Various brain regions are dissected and rapidly frozen and maintained at −70° C. until used.

Hippocampal tissue is dissected and homogenized on ice in 40 vols of buffer (50 mM Tris HCl, pH=7.7) using a Polytron homogenizer at setting 5 for 3×15 sec bursts. The homogenate is then centrifuged at 20,000 rpm (RC5-B; 50,000 g) and the supernatant discarded. The pellet is resuspended in 40 vols of the same buffer and incubated at 37° C. for 10 minutes to aid in the removal of endogenous serotonin. the homogenate is then centrifuged (as above) and the supernatant discarded. The pellet is then resuspended in 100 vols of buffer B (50 mM Tris HCl, pH=7.7 containing 0.1% ascorbate, 10 µM pargyline and 4 mM CaCl$_2$) and sonicated. An aliquot is taken for protein determination by the Lowry method and the remainder stored frozen at −70° C. until used.

The homogenate (50 µl; 0.4-0.6 mg protein/sample) is incubated with 100 µl (1.5-1.8 nM) 3H-8-hydroxy-2-(di-n-propylamino)tetraline in a final volume of 2 ml of buffer for 10 minutes at 37° C. At the end of the incubation, 3 ml of cold buffer A are added to each tube, and the contents rapidly filtered through Whatman GF/B glass filters. The filters are then rapidly washed 2 times with 3 ml of the same buffer, placed in scintillation vials, and shaken for 15 minutes with 10 ml of Hydrofluor (National Diagnostics) scintillation cocktail. The vials are then counted in a Packard 460 CD scintillation counter.

Specific binding is calculated for each of the treatment protocols and is defined as total binding less binding in the presence of excess unlabeled serotonin (1 µM). Specific binding obtained in vehicle-treated rats is compared to that obtained in animals receiving a single or various doses of test compound and expressed as percent of control. These results are then plotted as logit % binding vs. log concentration of test drug. Linear regression analysis then yields a straight line with 95% confidence limits from which an IC$_{50}$ can be inversely predicted. K$_i$ (inhibition constant) for the test drug is then calculated by the formula:

$$K_i = \frac{IC_{50}}{1 + \frac{[^3H-8-OH\ DPAT]}{K_D}}$$

where $K_D$ = 1.8 nm for 8-OH DPAT binding in hippocampus

The use of several doses of test compound also permits the calculation of an ID$_{50}$ value, i.e. an inhibitory dose that displaces 50% of the specific binding ex vivo.

Under these conditions, buspirone (30 mg/kg) displaced 46% of specific 3H-8-OH-DPAT binding from hippocampal membranes.

When tested in this assay, the compounds of the invention gave the following results.

TABLE 3

| Compound of Example No. | Inhibition Constant ($K_i$ nm) |
| --- | --- |
| 1 | 14 |
| 3 | 12 |
| 4 | 7 |

The results show that compounds of the invention have a moderate to extremely strong affinity for binding to the 5-HT-1A receptor site, evidencing a high potential for anxiolytic activity.

What is claimed is:

1. A compound having the formula $$\underset{O}{\overset{O}{\underset{\|}{\overset{\|}{R}}}}\diagdown N-(CH_2)_m-N\diagup\diagdown N-R^1\diagup(CH_2)_n$$

wherein R represents

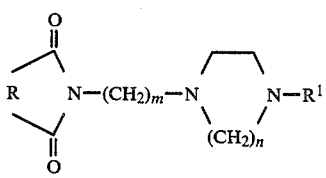,

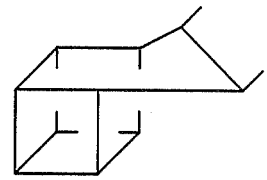, or

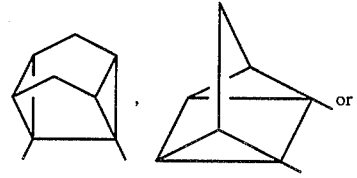

in which Y and Z are both

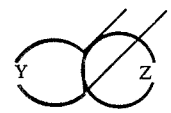

where X is methylene, ethylene or O and the dotted line represents an optional double bond, or one of Y or Z is

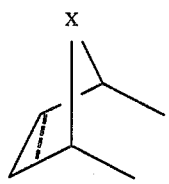

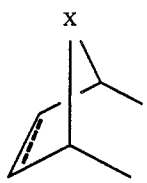

and the other represents —$(CH_2)_o$— or

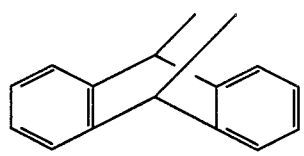

$R^1$ is unsubstituted or substituted phenyl, 2-pyridinyl, 2-pyrimidinyl, 2-pyrazinyl or 3-pyridazinyl, where the substituents are selected from the group lower alkyl, lower alkoxy, halo, cyano, nitro, hydroxy and trifluoromethyl;

m is 2–4;

n is 1–3;

o is 1–5;

and the pharmaceutically acceptable salts thereof.

2. A compound having the formula

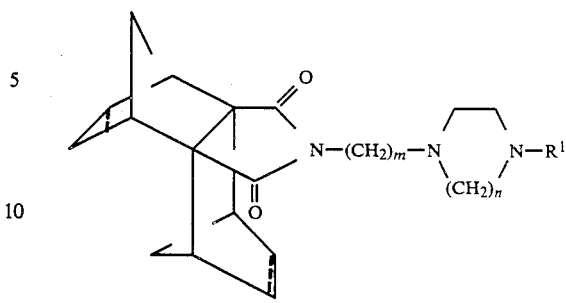

wherein
the dotted line represents an optional double bond;
$R^1$ is unsubstituted or substituted phenyl, 2-pyrazinyl or 3-pyridazinyl, where the substituents are selected from the group lower alkyl, lower alkoxy, halo, cyano, nitro, hydroxy and trifluoromethyl;
m is 2–4;
n is 1–3;
and the pharmaceutically acceptable salts thereof.

3. The compound of claim 1, having the name 1,4,5,8-tetrahydro-10-[4-[4-(2-pyrimidinyl-1-piperazinyl]butyl]-4a,8a-(methaniminomethano)-1,4:5,8-dimethanonaphthalene-9,11-dione.

4. The compound of claim 1, having the name 10-[4-[4-(6-chloro-2-pyrazinyl)-1-piperazinyl]butyl]-1,4,5,8-tetrahydro-4a,8a-(methaniminomethano)-1,4:5,8-dimethanonaphthalene-9,11-dione.

5. The compound of claim 1, having the name 1,4,5,8-tetrahydro-10-[4-[4-(2-pyrazinyl)-1-piperazinyl]butyl]-4a,8a-(methaniminomethano)-1,4:5,8-dimethanonaphthalene-9,11-dione.

6. The compound of claim 1, having the name octahydro-10-[4-[4-(2-pyrimidinyl)-1-piperazinyl]butyl]-4a,8a-(methaniminomethano)-1,4:5,8-dimethanonaphthalene-9,11-dione.

7. The compound of claim 1, having the name octahydro-10-[4-[4-(6-chloro-2-pyrazinyl)-1-piperazinyl]butyl]-4a,8a-(methaniminomethano)-1,4:5,8-dimethanonaphthalene-9,11-dione.

* * * * *